US010551290B2

(12) United States Patent
Quillien et al.

(10) Patent No.: US 10,551,290 B2
(45) Date of Patent: Feb. 4, 2020

(54) DEVICE FOR MEASURING AND CONTROLLING ON-LINE VISCOSITY AT HIGH PRESSURE

(71) Applicants: Bernard Quillien, Sorbiers (FR); Emmanuel Pich, La Talaudiere (FR)

(72) Inventors: Bernard Quillien, Sorbiers (FR); Emmanuel Pich, La Talaudiere (FR)

(73) Assignee: S.P.C.M. SA (FR)

(*) Notice: Subject to any disclaimer, the term of this patent is extended or adjusted under 35 U.S.C. 154(b) by 176 days.

(21) Appl. No.: 14/040,281

(22) Filed: Sep. 27, 2013

(65) Prior Publication Data

US 2014/0053637 A1 Feb. 27, 2014

Related U.S. Application Data

(63) Continuation of application No. PCT/EP2012/056593, filed on Apr. 11, 2012.
(Continued)

(30) Foreign Application Priority Data

Apr. 11, 2011 (FR) ................................. 11 53117

(51) Int. Cl.
*G01N 11/00* (2006.01)
*E21B 21/06* (2006.01)
(Continued)

(52) U.S. Cl.
CPC ............ *G01N 11/00* (2013.01); *E21B 21/062* (2013.01); *E21B 43/16* (2013.01); *E21B 43/20* (2013.01);
(Continued)

(58) Field of Classification Search
CPC ...... G01N 11/00; G01N 1/2035; G01N 11/08; G01N 2001/205; G01N 2001/2064;
(Continued)

(56) References Cited

U.S. PATENT DOCUMENTS 3,548,638 A * 12/1970 Yasumasa ............... G01N 11/08
73/54.09
4,041,708 A * 8/1977 Wolff ...................... F04D 31/00
60/649
(Continued)

FOREIGN PATENT DOCUMENTS

| EP | 1431713 A1 | 6/2004 |
| FR | 2922256 A1 | 4/2009 |
| FR | 2948964 A1 | 2/2011 |

OTHER PUBLICATIONS

Kawasetsu et al., Tube body for pressure transducer, 2010, ProQuest Technology Research Professional.*
(Continued)

*Primary Examiner* — John Fitzgerald
*Assistant Examiner* — Truong D Phan
(74) *Attorney, Agent, or Firm* — Forge IP, PLLC

(57) ABSTRACT

Device that can be used in an enhanced oil recovery method by injection of a solution of water soluble polymer and brine having a viscosity below 1000 cps that includes a mixer, and preferably a static mixer, capable of homogenizing the solution on-line; a device capable of measuring the viscosity of the homogenized solution, continuously, downstream of the solution injection pump, at a pressure below or equal to 250 bars, and preferably between 50 and 250 bars, and at a temperature below or equal to 120° C., and preferably between 40 and 120° C., by measuring a pressure drop in a calibrated tube, at a constant rate of flow.

18 Claims, 2 Drawing Sheets

Related U.S. Application Data

(60) Provisional application No. 61/476,635, filed on Apr. 18, 2011.

(51) Int. Cl.
| | | |
|---|---|---|
| *G01N 1/20* | (2006.01) | |
| *E21B 47/10* | (2012.01) | |
| *E21B 43/20* | (2006.01) | |
| *E21B 43/16* | (2006.01) | |
| *G01N 11/08* | (2006.01) | |

(52) U.S. Cl.
CPC ........... *E21B 47/10* (2013.01); *G01N 1/2035* (2013.01); *G01N 11/08* (2013.01); *G01N 2001/205* (2013.01); *G01N 2001/2064* (2013.01)

(58) Field of Classification Search
CPC ........ E21B 43/16; E21B 21/062; E21B 47/10; E21B 43/20
USPC .............................................. 73/54.01; 137/92
See application file for complete search history.

(56) References Cited

U.S. PATENT DOCUMENTS

| | | | | |
|---|---|---|---|---|
| 4,249,608 A * | 2/1981 | Carter | ................... | C09K 8/905 166/246 |
| 4,395,340 A * | 7/1983 | McLaughlin | ............. | C08F 2/10 166/266 |
| 4,603,154 A * | 7/1986 | Luetzelschwab | ........ | B01J 14/00 523/313 |
| 4,627,271 A * | 12/1986 | Abbott | ................... | G01N 11/08 73/54.06 |
| 4,821,564 A | 4/1989 | Pearson et al. | | |
| 4,876,882 A * | 10/1989 | Yau | ........................ | G01N 11/08 73/54.01 |
| 4,945,992 A * | 8/1990 | Sacco | ........................ | C02F 1/76 166/310 |
| 5,129,457 A * | 7/1992 | Sydansk | ............... | E21B 43/168 166/268 |
| 5,164,099 A * | 11/1992 | Gupta | ...................... | C09K 8/62 166/300 |
| 5,172,585 A * | 12/1992 | Gleissle | ................. | G01N 11/08 73/54.04 |
| 5,283,001 A * | 2/1994 | Gregoli | ................. | B01F 3/0807 137/13 |
| 5,304,001 A * | 4/1994 | Kuo | .................... | B01F 15/0412 366/132 |
| 5,969,733 A * | 10/1999 | Sheinman | .................. | B41J 2/02 347/75 |
| 6,079,198 A * | 6/2000 | Prowse | .................... | F02C 7/228 60/734 |
| 6,339,959 B1 * | 1/2002 | Natapov | ................... | G01F 1/28 73/239 |
| 6,386,016 B1 * | 5/2002 | Gleissle | ................. | G01N 11/08 73/54.01 |
| 7,318,474 B2 * | 1/2008 | Welton | ................... | C09K 8/508 166/280.1 |
| 2003/0077299 A1 * | 4/2003 | Iwai | ....................... | A61K 8/062 424/400 |
| 2003/0164439 A1 * | 9/2003 | Verbrugge | .............. | B29C 33/42 249/175 |
| 2006/0276347 A1 * | 12/2006 | Lin | ......................... | C09K 8/58 507/209 |
| 2007/0256736 A1 * | 11/2007 | Tonkovich | ............ | B01F 3/0807 137/92 |
| 2009/0090504 A1 | 4/2009 | Weightman et al. | | |
| 2009/0137429 A1 * | 5/2009 | Rimassa | .................. | C09K 8/03 507/201 |
| 2009/0241678 A1 * | 10/2009 | Motoyama | ............ | G01L 9/0033 73/717 |
| 2009/0320599 A1 * | 12/2009 | Burat | ................... | G01N 29/043 73/622 |
| 2010/0126717 A1 * | 5/2010 | Kuchuk | ................ | E21B 49/008 166/250.03 |
| 2010/0248336 A1 * | 9/2010 | Bridenbaugh | ........... | C07H 1/06 435/270 |
| 2011/0048378 A1 * | 3/2011 | Song | .................. | F02M 37/0023 123/445 |
| 2011/0092394 A1 * | 4/2011 | Peng | ...................... | C07D 213/20 507/102 |
| 2011/0226472 A1 * | 9/2011 | Kieffer | ...................... | F17D 1/17 166/270.1 |
| 2011/0297399 A1 * | 12/2011 | Dyck | ...................... | E21B 43/16 166/386 |
| 2012/0127466 A1 * | 5/2012 | Karnes | ................... | G01N 11/04 356/319 |
| 2012/0292025 A1 * | 11/2012 | Stoll | ....................... | E21B 43/16 166/269 |
| 2013/0118235 A1 * | 5/2013 | Morgan | ................. | G01N 11/14 73/54.28 |
| 2014/0004605 A1 * | 1/2014 | Donohue | ................. | C10L 1/02 435/410 |

OTHER PUBLICATIONS

Richard et al., A Circulating Foam Loop for Evaluating Foam at Conditions of Use, Feb. 2003, Society of Petroleum Engineers, SPE 80242, pp. 1-10.*
International Preliminary Report on Patentability Application No. PCT/EP2012/056593 Completed: May 24, 2013 13 pages.
International Search Report and Written Opinion of the International Searching Authority Application No. PCT/EP2012/056593 Completed: Jun. 27, 2012; dated Jul. 6, 2012 10 pages.

* cited by examiner

DEVICE FOR MEASURING AND CONTROLLING ON-LINE VISCOSITY AT HIGH PRESSURE

FIELD OF THE INVENTION

The object of the invention is a device for measuring and controlling on-line viscosity at high pressure.

BACKGROUND OF THE INVENTION

Different petroleum production methods can be employed as appropriate. These are mainly:
primary production relative to the spontaneous production of petroleum by internal pressure in the reservoir;
secondary production where the internal pressure in the reservoir is maintained by water injection; and
tertiary production comprising different enhanced recovery methods.

The appropriate method is selected as a function of the required investment (capex) and operational costs (opex) which are themselves related to the type of oil, the type of reservoir and to the viscosity of the oil.

The numerous enhanced oil recovery methods employed in an oil field have each their advantages. Among these methods, the following may be cited in particular:
re-injection of the gas produced;
injection of carbon dioxide with the additional purpose of fixing same to avoid the greenhouse effect;
injection of different solvents;
steam heating for heavy oils;
injection of bases for acid oils;
injection of surfactants;
in situ combustions by injecting oxygen;
biological methods with formation of bio-surfactants;
electric field diffusion methods etc.

One of the most simple and effective methods comprises injecting a viscous aqueous solution.

The solution is made viscous by dissolution of water soluble polymers, and particularly polyacrylamides, xanthan gums, and more anecdotally, guar gums or cellulose ethers.

Polyacrylamides constitute the preferred additives since they have very high resistance to biodegradation while xanthan gums require the use of strong doses of toxic bactericides, and particularly formaldehyde.

In general, the enhanced oil recovery method by polymer injection mainly comprises:
dissolving the polyacrylamide, delivered in powder or emulsion form, at a high concentration of between 5 and 20 g/L for example, in water or a desoxygenated brine (to prevent its degradation);
injecting this mother solution into the water or brine injection pipeline and injecting the resulting mixture into the well under consideration.

The particular objective is to maintain a constant viscosity during the injection of the water soluble polymer solution, so that the reservoir can be swept efficiently.

It is now known how to measure on-line and continuously the viscosity of the mother solution with some accuracy, particularly with Brookfield viscometres. This measurement is possible even if the solution is highly viscous and has a degree of heterogeneity, due particularly, on the one hand, to the presence of measurement-distorting gas bubbles and, on the other hand, due to the variation of the viscosity in the same conditions of concentration as a function of the salinity.

The variations in flow rates and salinities inherent in industrial processes make it necessary to measure the viscosity on injection.

This may be done by taking samples under API (American Petroleum Institute) conditions in order to prevent mechanical degradation due to the rapid decompression of the solution.

However, to the knowledge of the Applicant, there is no device in existence for measuring the viscosity at the time of injection, when the pressure in the pipeline generally varies between 50 and 250 bars in enhanced oil recovery processes.

Prior art viscometres include:
FORD or ZAHN cup viscometres, consistometres, falling ball viscometres working at atmospheric pressure;
Brookfield rotary viscometres which can be put on-line but in respect of which, above some pressures, mechanical deformation phenomena distort the measurement. They are used up to 50 bars, and exceptionally 70 bars of pressure;
vibration viscometres that rise to slightly higher pressures but in respect of which the shear of the non-Newtonian solution gives random results that cannot be correlated with the Brookfield viscosities measured in the laboratory;
oscillating piston viscometres that have the same characteristics as vibration viscometres;
capillary viscometres, discontinuous devices that measure very low speeds and therefore very low shears. Only the Brookfield device allows extrapolations to similar although higher shears.

Documents US 2009/0090504 and U.S. Pat. No. 4,821,564 describe devices for measuring the viscosity of an injection solution by measuring a pressure drop. However, as the viscosity is measured upstream of the injection pump, these devices are not designed for use at the injection pressure but pressures much lower than 50 bars.

The problem the invention proposes to solve is that of perfecting an on-line device for measuring, in high pressure conditions of between 50 and 250 bars, viscosities below 1000 cps that can be correlated with the Brookfield viscosities measured in the laboratory also known as "Yield Viscosity".

SUMMARY OF THE INVENTION

The Applicant has developed a device or set of equipment that can be used to measure the viscosity of an injection solution continuously and downstream of the injection pump, as long as the following two conditions are met:
satisfactory homogeneity of the polymer solution. Indeed, it is very difficult to mix about 1 part by weight of highly viscous mother solution with 9 parts by weight of brine in an injection tube working at a flow rate of between 4 and 100 m3 per hour, with a speed of between 2 and 5 metres per second. In most solutions proposed in the prior art, homogeneity is only partially obtained in the injection surfaces, after a few thousand metres of pipeline and a few thousand metres of injection tubes;
a device giving a viscosity that can be extrapolated as Yield Viscosity, in other words with low shear and allowing measurements at extremely high pressures, in other words up to 250 bars, the device comprising materials that resist corrosion at the injection temperatures (40 to 120° C.).

To be more specific, the invention is a device that can be used in an enhanced oil recovery method by injection of a solution of water soluble polymer or brine having a viscosity below 1000 cps, including:
- a mixer, preferably a static one, capable of homogenizing the solution on-line;
- a device capable of measuring the viscosity of the homogenized solution, continuously, downstream of the solution injection pump at a pressure below or equal to 250 bars, preferably between 50 and 250 bars, and at a temperature below or equal to 120° C., and preferably between 40° and 120° C., by measuring a pressure drop in a calibrated tube, at a constant rate of flow.

In the inventive device, associating these two pieces of mixing and measuring equipment gives a satisfactory and reliable measurement of the viscosity, after mixing, of the mother solution and of the brine, high pressure (in practice between 50 and 250 bars).

The static mixer can be used in particular to homogenize the polymer solution, at the injection pressure, before measuring its viscosity.

The Mixer

Homogenizing the solution by mixing requires a specific designed mixer that mixes the solution and limits mechanical degradation of the polymer, which is very shear-sensitive.

The mixer is preferably placed downstream of the injection pump, but obviously upstream of the device capable of measuring the viscosity of the solution injected.

A dynamic mixer may for example be used that comprises a rotor with low shear so that the mother solution is able to be incorporated into the brine. Experience shows that the rotor must not exceed a speed of 6 metres per second at the very most, which can be obtained with a low speed and high flow rate centrifugal pump. However, the residence time is short, which induces the use of a plurality of pumps in series or a multi-cellular pump. Although it is technically possible, the cost at high flow rate or high pressure is not economically viable.

In one advantageous embodiment, the mixer is a static mixer of the same type as those marketed by the companies Sulzer Chemtech 25 Ltd-Sulzer-Allee 48-CH 8404 Winterthur-Switzerland for Europe and Kenics, Chemineer Inc, 125 Flagship Drive, North Andover, Mass. 01845 USA. The static mixer is preferably of the same type as those specifically described in the document EP1437173, and marketed by SULZER under the names SMX and SMV. The use of a static mixer in an enhanced oil recovery process is described in particular in the document FR 2 922 256.

Preferably, the static mixer includes at least one unitary mixing component with a lattice work structure. Each mixing component includes an external cylindrical body enclosing the mixing components themselves, which come in the form of a specific lattice work structure. The diameter of the mixing components is variable, and can be adjusted as a function of the pressure drop they generate. The static mixer preferentially generates a pressure drop of between 1 and 5 bars, and preferably between 2 and 3 bars.

The static mixer includes preferably between 10 and 50 mixing components, and more preferably between 20 and 30 mixing components, the diameter thereof being preferably about 10 mm.

In a preferred embodiment of the invention, the rate at which the water soluble polymer injection solution flows in the static mixer is between 1 and 5 m/s, and preferably 3 m/s.

Device Capable of Measuring the Viscosity

The device capable of measuring the viscosity combines:
- a pump, the flow rate thereof being controlled by a speed variator or a regulation valve,
- a calibrated tube creating a pressure drop,
- a precision Coriolis effect mass flow meter, with oval gears or with less electromagnetic precision,
- a high-precision device for measuring differential pressure in the range 0-10 bars that is resistant to both corrosion and line pressures,
- optionally a duplex filter with a 10-micron mesh, for example, so that suspended matter that may block the pump or the oval wheel flow meter can be eliminated,
- optionally, a main line pulse absorber.

Preferably the device capable of measuring the viscosity is placed in a bypass of the main pipe in which the injection solution flows. The sample is directly taken in the main pipe under high pressure and reinjected into said pipe, also under high pressure.

The pump is preferably a volumetric pump and in this case it is associated with a precision flow meter and with a speed variator. But the pump may also be centrifugal in the case of low pressures (below 100 bars) and in this case it is associated with a flow meter and a regulation valve. The pump is preferably placed upstream of the tube and, in practice, it has a flow rate of 20 l/hr for example.

The pump, the tube, the flow meter, the differential pressure measurement device, the speed variator, the regulation valve and any pulse absorber are capable of resisting pressures of 250 bars. They are manufactured preferably from a material selected from the group that includes:
- austeno-ferritic steels, and preferably austeno-ferritic steels containing between 24 and 26% of chromium and between 6 and 8% of nickel;
- super alloys mainly containing nickel, but also a plurality of metals such as chromium, magnesium, iron and titanium (Hastelloy).

These materials make it possible to work with all brine compositions encountered in the field.

In practice, the calibrated tube comes at least partly in the form of a coil.

In one preferred embodiment, the calibrated tube measures 20 metres in length for an internal diameter of 10 mm, the wall having a thickness of 4 mm. Its dimensions may be modified by those skilled in the art on condition they allow for a sufficient pressure drop that can be measured by the differential pressure measurement device.

In general, the device capable of measuring the viscosity may be used to measure a pressure drop while limiting the shear of the polymer.

The inventive device can measure viscosities between 1 and 1000 cps, preferably 5 to 100 cps.

The differential pressure measurement device can be used to measure the pressure drop in the calibrated tube below 2 bars when the static (injection) pressure is below or equal to 250 bars. In general, the pressure drop generated by the calibrated tube is between 0.01 and 2 bars. As already specified, those skilled in the art would know how to adjust the dimensions of the calibrated tube as a function of the pressure drop.

According to the invention, the pressure drop measured under high pressure in the calibrated tube can be extrapolated to the corresponding viscosity of the water soluble polymer solution, measured at atmospheric pressure in a Brookfield device in the same conditions of concentration and salinity. As has already been said, the viscosity of the solution can be extrapolated as Yield Viscosity, in other words with low shear.

In order to obtain correct correlations, it is important for the shear rates in the calibrated tube to be low and similar to those observed with a Brookfield viscometre which is a device widely used in the water soluble polymer industry, as well as in enhanced oil recovery applications.

To be more specific, the shear rate in the calibrated tube is preferably between $10\ s^{-1}$ and $500\ s^{-1}$, and more preferably between $50\ s^{-1}$ and $200\ s^{-1}$.

The shear rates in the calibrated tube are therefore considered as low and this is made possible thanks to a low speed flow of fluid in the calibrated tube, under high pressure.

Document U.S. Pat. No. 3,548,638 discloses devices capable of measuring the viscosity of fluids at high pressure and at high temperatures which are specific to the introduction of fluids with extremely high viscosities, generally of at least 1 million cps. The pressure drops measured are approximately 150 bars and the fluid goes through a small diameter cross section. This results in extremely high shear rates (well above $10,000\ s^{-1}$) which makes the use of this type of device totally incompatible in an enhanced oil recovery installation in which the viscosity is measured continuously. Indeed, the acrylamide polymers commonly used in enhanced oil recovery techniques would then be greatly damaged in terms of the shear, which would render any viscosity measurement completely false.

The pulse absorber is preferably downstream of the pump of the device. Upstream of the pump is the duplex filter. They are placed preferably in the bypass of the main pipe.

The device can be isolated from the main pipe by two valves.

This invention also relates to a method for measuring, continuously, the viscosity of the injection solution of an aqueous solution of water soluble polymer under high pressure, of between 50 and 250 bars in an enhanced oil recovery method, downstream of the injection pump. It is used in particular to measure the pressure drop corresponding to the pressure drop in the calibrated tube. This pressure drop is then correlated with the corresponding viscosity of the solution measured at atmospheric pressure, using a Brookfield device in the same conditions of salinity and concentration. This method employs the device as described above.

The invention and the resulting advantages thereof will become clearer from the following figures and examples, provided to illustrate the invention and non-restrictively.

DETAILED DESCRIPTION OF THE INVENTION

Figure 1:
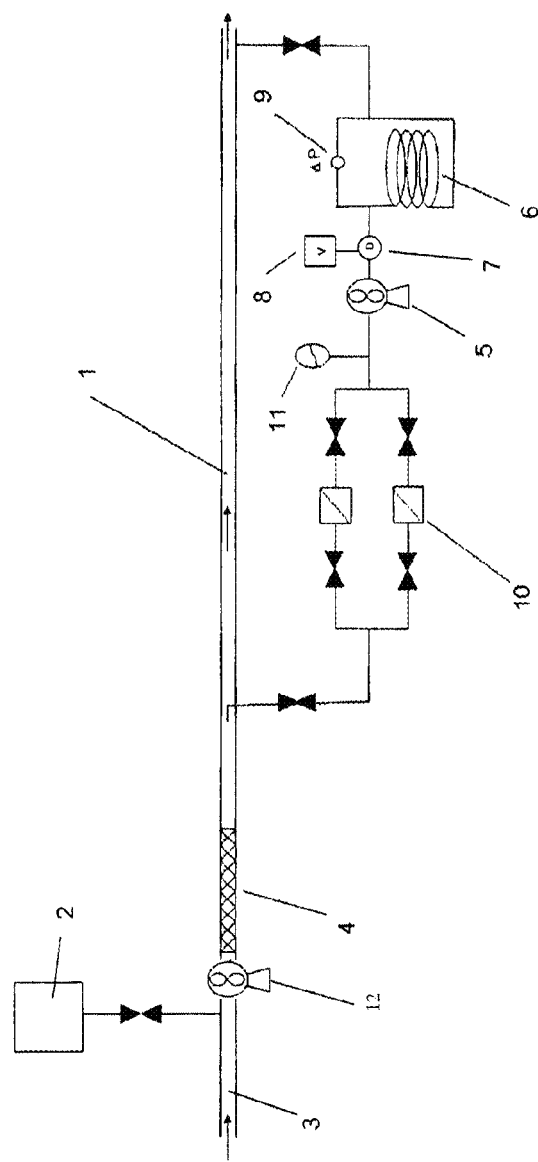
FIG. 1 shows a device in accordance with this invention including in particular a bypass, installed on a pipe for the injection of a solution containing a water soluble polymer into an enhanced oil recovery facility.

The inventive device is specially constructed so that it can be used at high well pressures, with a low speed measurement that can be extrapolated as Brookfield viscosity (Yield Viscosity), in materials that are corrosion-resistant in injection conditions.

It includes in particular on the main pipe (1) for the injection, via a solution injection pump (12), of the mother solution (2) previously diluted with injection brine water (3):
    a static mixer (4) (marketed by SULZER under the names SMX or SMV) including 25 components
on a bypass of the main pipe (1):
    a positive displacement pump (5) (which may also be a centrifugal pump) with a flow rate of 20 litres per hour, manufactured in Super Duplex or Hastelloy;
    a tube (6) in Super Duplex, 10 mm in internal diameter and 4 mm thick resistant to 250 bars of pressure and 20 metres in length;
    a precision Coriolis effect mass flow meter (7) in Super Duplex, with oval gears or with less electromagnetic precision,
    a speed variator (8) for adjusting the speed to the required rate of flow;
    a high-precision differential pressure measurement device (9) in the range 0-10 bars and resistant to both corrosion and line pressures;
    a duplex filter (10) with a 10-micron mesh, for example, so that suspended matter that may block the pump or the oval wheel flow meter can be eliminated; and
    a main line pulse absorber (11).

To fill this device, the solution is sampled at the centre of the injection tube so that it can be re-injected into the same line. It is in fact a continuous device with no discharge into the atmosphere.

Figure 2:
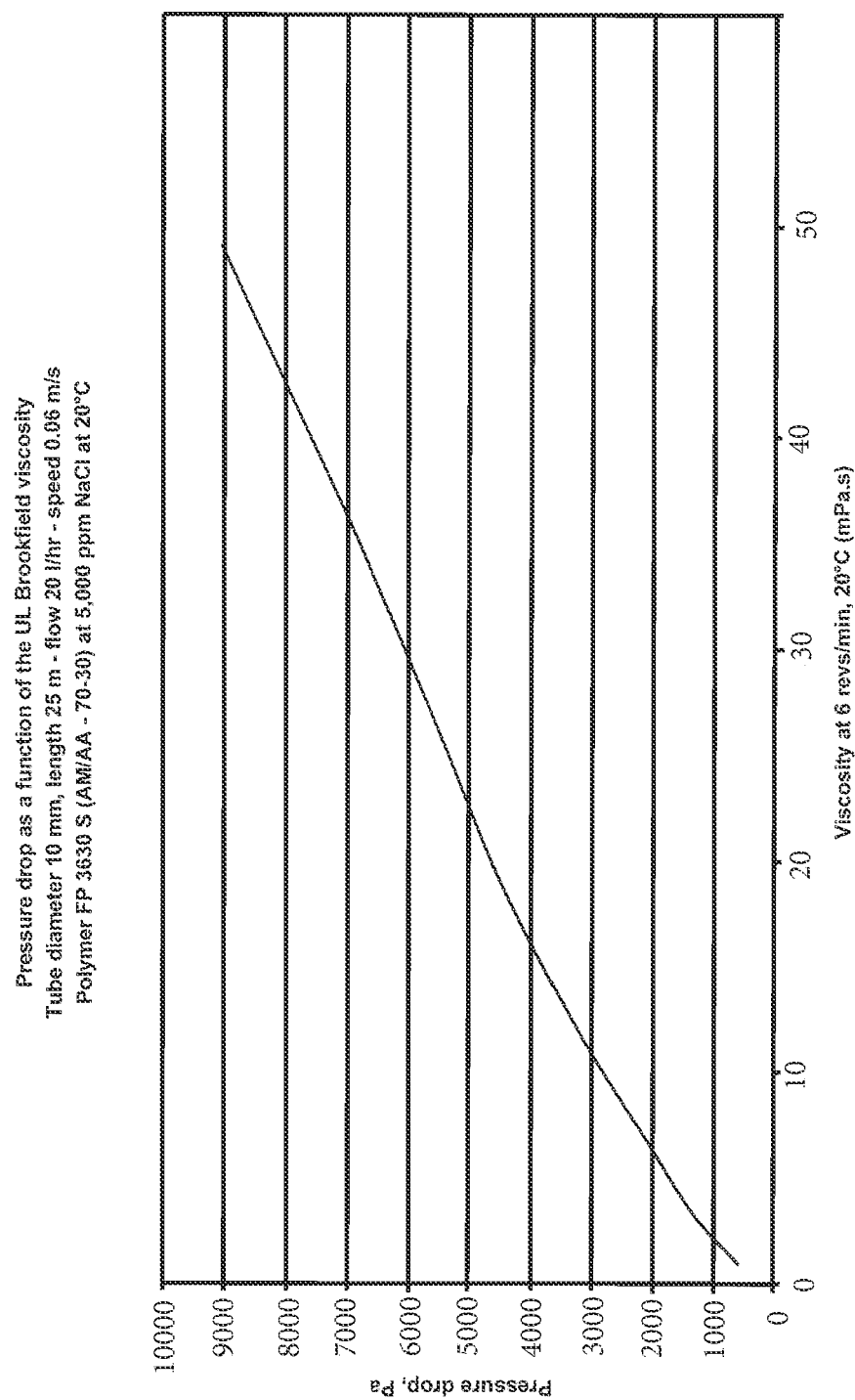
FIG. 2 shows the pressure drop measured in respect of a solution of water soluble polymer as a function of its viscosity.

This device has been tested comparatively to Brookfield measurements on solutions of polymers of different viscosities with the results in the curve in FIG. 2. To be more specific it shows the pressure drop observed as a function of the UL viscosity of a solution of an acrylamide/acrylic acid copolymer (70/30 in mole) sheared at $60\ s^{-1}$, in a brine containing 5000 ppm of NaCl, at 20° C. The UL viscosity is measured using a Brookfield device (LV module 6 rpm)

Under these conditions sufficient correlation is then obtained between pressure drop and viscosity. This then makes it possible to:
    record the injection viscosities,
    modify the mother solution flow rate so as to control the flow rate of the volumetric pump and thereby maintain the required viscosity of the solution.

The inventive device may therefore be used to measure viscosities in the range between 1 and 1000 cps, and preferentially between 5 and 100 cps.

Those skilled in the art may adapt the equipment for different conditions or purposes. It may be possible for example to:
    increase the tube length so as to increase measurement accuracy;
    increase the flow rate so as to increase precision at low viscosity;
    reduce the flow rate for highly viscous solutions that are used for example for highly viscous oils;
    change the flow rate of the pump and the diameter of the measurement tube etc.

What is claimed is:

1. A device adapted for use in an enhanced oil recovery method by injection through a main pipe, via a solution injection pump, of a solution of water soluble polymer and brine having a viscosity below 1000 cps, including:
    the main pipe and the solution injection pump coupled to the main pipe;
    a static mixer capable of homogenizing the solution inline, the static mixer including at least one unitary mixing component with a lattice work structure, and between 10 and 50 mixing components, a diameter of the static mixer being about 10 mm;

a device capable of measuring the viscosity of the homogenized solution, continuously, downstream of the solution injection pump, at a pressure between 50 and 250 bars, and at a temperature below or equal to 120° C., by measuring a pressure drop in a scaled tube, at a constant rate of flow;

wherein the device capable of measuring the viscosity is placed in a bypass of the main pipe in which the injection solution flows;

wherein the device capable of measuring the viscosity comprises a measuring device pump, a flow rate of the measuring device pump being controllable independently of a flow rate of the solution injection pump;

wherein a speed at which the water soluble polymer injection solution flows in the static mixer is between 1 and 5 m/s; and wherein a pressure drop in the static mixer is between 1 and 5 bars.

2. The device of claim 1 wherein the temperature is between 40 and 120° C.

3. The device of claim 1 wherein the static mixer includes between 20 and 30 mixing components.

4. The device of claim 1 wherein the speed at which the water soluble polymer injection solution flows in the static mixer is 3 m/s.

5. The device of claim 1 wherein the pressure drop in the static mixer is between 2 and 3 bars.

6. The device of claim 1 wherein a shear rate in the scaled tube is between 10 $s^{-1}$ and 500 $s^{-1}$.

7. The device of claim 6 wherein the shear rate in the scaled tube is between 50 $s^{-1}$ and 200 $s^{-1}$.

8. A method for continuously measuring the viscosity of an aqueous solution of water soluble polymer under high pressure, of between 50 and 250 bars, in an enhanced oil recovery method, downstream of an injection pump employing the device of claim 1.

9. The method of claim 8 comprising measuring the pressure drop corresponding to the pressure drop in the scaled tube, a pressure drop that is correlated with the corresponding viscosity of the solution measured at atmospheric pressure, using a Brookfield device in the same conditions of salinity and concentration.

10. The device of claim 1 wherein the flow rate of the measuring device pump is controlled by a speed variator or a regulation valve and the device capable of measuring the viscosity further includes:
    a scaled tube creating a pressure drop,
    a flow meter, wherein the flow meter comprises a precision Coriolis effect mass flow meter, an oval wheel flow meter or an electromagnetic flow meter, and
    a differential pressure measurement device resistant to both corrosion and line pressures.

11. The device of claim 10 wherein the measuring device pump is a positive displacement pump and its flow rate is controlled by a flow meter connected to a speed variator.

12. The device of claim 10 wherein the measuring device pump is a centrifugal pump with the flow rate thereof being controlled by a flow meter associated with a regulation valve.

13. The device of claim 10 wherein the scaled tube measures 20 metres in length for an internal diameter of 10 mm, and whereof the wall is 4 mm thick.

14. The device of claim 10 wherein the pressure drop measured in the scaled tube is extrapolated to the corresponding viscosity of the water soluble polymer solution, measured at atmospheric pressure in a Brookfield device in the same conditions of concentration and salinity.

15. The device of claim 10 wherein the device capable of measuring the viscosity further includes:
    a duplex filter with a mesh, adapted to eliminate suspended matter that may block the measuring device pump or the flow meter,
    a main line pulse absorber.

16. The device of claim 15 wherein the mesh is a 10 microns mesh.

17. The device of claim 10 wherein the measuring device pump, the tube, the flow meter, the differential pressure measurement device, the speed variator, the regulation valve and any pulse absorber are capable of resisting pressures of up to 250 bars.

18. The device of claim 17 wherein the measuring device pump, the tube, the flow meter, the differential pressure measurement device, the speed variator, the regulation valve and any pulse absorber are manufactured in a material selected from the following:
    austeno-ferritic steels, and;
    super alloys mainly containing nickel.

* * * * *